United States Patent

Anner et al.

[11] 4,054,563
[45] Oct. 18, 1977

[54] PROCESS FOR THE MANUFACTURE OF SPIRO COMPOUNDS OF THE STEROID SERIES

[75] Inventors: Georg Anner, Basel; Adrian Marxer, Muttenz; Charles Meystre; Hansuli Wehrli, both of Reinach, all of Switzerland

[73] Assignee: Ciba-Geigy Corporation, Ardsley, N.Y.

[21] Appl. No.: 677,358

[22] Filed: Apr. 15, 1976

[30] Foreign Application Priority Data

Apr. 25, 1975 Switzerland .................. 5375/75
Oct. 2, 1975 Switzerland .................. 12788/75

[51] Int. Cl.² ..................................... C07J 71/00
[52] U.S. Cl. ..................... 260/239.55 R; 260/397.5; 260/397.45
[58] Field of Search ................. 260/397.5, 239.55

[56] References Cited

U.S. PATENT DOCUMENTS

| 3,254,074 | 5/1966 | Arth et al. | 260/239.55 |
| 3,364,207 | 1/1968 | Brown | 260/239.55 |
| 3,798,213 | 3/1974 | Arth | 260/397.5 |

Primary Examiner—Elbert L. Roberts
Attorney, Agent, or Firm—Theodor O. Groeger

[57] ABSTRACT

Compounds of the general formula

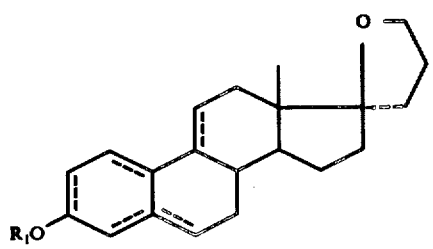

(I)

wherein $R_1$ represents a hydrogen atom or a lower alkyl group, which contain a double bond in 5-position and a methyl group in 10-position, or three double bonds in the position 1,3 and 5(10), and which can contain an additional double bond in the 9(11)-position, are manufactured by a novel process, in which a 17-oxosteroid of the general formula

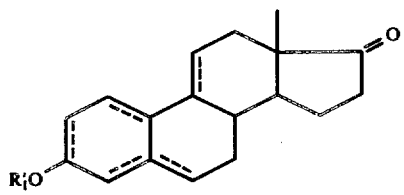

(II)

wherein $R_1'$ represents a hydrogen atom, a lower alkyl group or an acyl group, and which contains double bonds and optionally a methyl group in the positions indicated above, is reacted with an organometallic compound of the formula

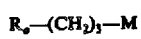

$R_o-(CH_2)_3-M$ (III)

wherein M represents a grouping MgX, in which X represents a halogen atom or an alkali metal atom and $R_o$ represents a di-lower alkylamino group, and the resultant 17β-hydroxy-17α-(γ-di-lower alkylaminopropyl) compound of the general formula

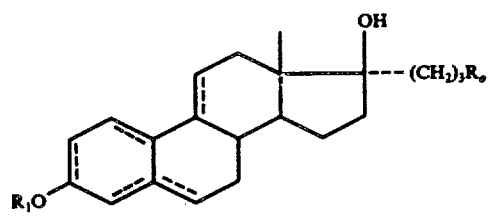

(IV)

wherein $R_1$ and $R_o$ are as defined in formulae (I) and (III) respectively and, which contains double bonds and optionally a methyl group in the positions indicated above, is deaminated with cyclization under the known conditions of the Hofmann elimination by converting into the corresponding quaternary tri-lower alkyl ammonium salt and decomposing this latter by heat in the form of the corresponding quaternary base.

7 Claims, No Drawings ized superior property characteristics from among those discussed.

1-(4-ACYLOXYALKYLAMINONAPHTHYLAZO)-4-NITROBENZENE DISPERSE DYES

CROSS-REFERENCE TO RELATED APPLICATION

This is a continuation-in-part of my copending patent application, Ser. No. 449,063, filed on Mar. 7, 1974 now abandoned.

BACKGROUND OF THE INVENTION

The invention dyes satisfy a long felt need in the disperse dye industry. They are tinctorially strong, navyblue monoazo dyes of low water solubility which are useful for dyeing and printing polyester, polyamide, and cellulose acetate substrates in any form. Each of the invention dyes has a balance of the desirable dye properties described hereafter. In addition to this balance of properties, each dye displays one or more unexpectedly superior property characteristics from among those discussed.

There are several publications disclosing disperse dyes which dyes, however, fail to provide the balance of properties displayed by the invention dyes. Such publications include U.S. Pat. Nos. 2,016,944, 2,045,324, 2,266,142, 2,359,305, and Japanese Pat. No. 47/35353. The invention dyes have good affinity, buildup and leveling properties on the above described substrates. They are relatively insensitive to temperature variations during dyeing and to the effects of trace metal contamination during dyeing. They are also resistant to hydrolysis during dyeing, notably in high temperature processes. The dyes provide finished dyeings exhibiting good fastness to light, to thermal fixation, to sublimation, and to pleating. The invention dyes provide dyeings having good wetfastness including fastness to water, to sea water, to washing, and to perspiration. The dyeings are also resistant to rubbing, and to the effects of ordinary solvents such as those used in drycleaning. Dyeings made with invention dyes also have good gas fume fastness such as resistance to ozone and to chlorine. Dyeings made with the invention dyes also have the ability to withstand the rigors of precure and postcure permanent press finishing and soil release finishing.

SUMMARY OF THE INVENTION

The new dyes correspond to the formula

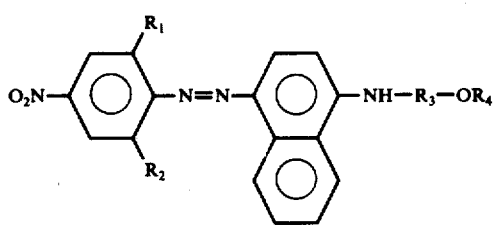

wherein
$R_1$ is Br, Cl or CN;
$R_2$ is CN or $NO_2$;
$R_3$ is $C_{2-4}$(branched or straight-chain)alkylene;
$R_4$ is cyclohexyl, $C_{1-4}$alkylcyclohexyl, benzyl or $C_{2-6}$(branched or straight-chain)alkylene-$R_5$;
$R_5$ is CN, $-OC_{1-4}$alkyl, $-OR_6$, $-OCOC_{1-4}$alkyl or $-OCOR_6$; and $R_6$ is phenyl or phenyl substituted with 1-2 groups selected from Cl, Br, $NO_2$, $C_{1-4}$alkyl, $OC_{1-4}$alkyl and $CF_3$.

Particularly preferred are the dyes wherein $R_1$ is Br or Cl; $R_2$ is $NO_2$; $R_3$ is $C_{2-4}$alkylene and $R_4$ is $C_{2-6}$ alkylene $OCOC_{1-4}$alkyl.

DETAILS OF THE INVENTION

The dyes of this invention are prepared by conventional diazotization and coupling procedures wherein a primary aromatic amine of the formula

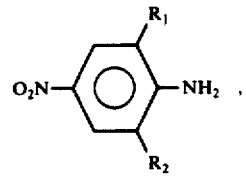

is diazotized and coupled to an aromatic amine of the formula

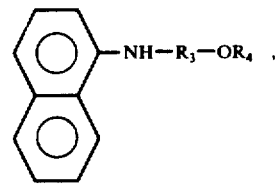

wherein $R_1$, $R_2$, $R_3$ and $R_4$ are as defined above. In the case wherein $R_4$ contains a readily hydrolyzable group, e.g., when $R_4$ is $C_{2-6}$alkylene-$OCOC_{1-4}$alkyl or $C_{2-6}$alkyleneOCOR$_6$, wherein $R_6$ is as defined above, coupling of the diazotized amine can also be made to an aromatic amine of the formula

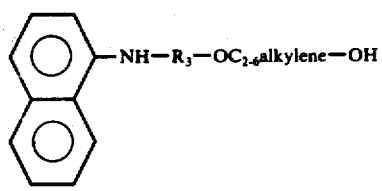

followed by acylation of the primary hydroxy group of the resultant monoazo compound by conventional techniques, for example, by treatment with an aliphatic or aromatic carboxylic acid chloride, bromide or anhydride to yield the desired dye.

The diazotization of the primary aromatic amine can be carried out at from 0° to 25° C, preferably at 20° to 25° C, by the action of nitrosylsulfuric acid in 70% to 80% aqueous sulfuric acid. Coupling is carried out by dissolving the aromatic amine coupler in an organic or aqueous-organic solvent system, such as a mixture of methanol and water, cooling the resultant coupler solution to 15° or less and then slowly adding the diazo solution to the cold coupler solution. After the coupling is complete, the disperse dye is precipitated by raising the pH to about 1 to 3 with a suitable salt or base, such as sodium acetate or sodium hydroxide. The precipitated monoazo dye is isolated by filtration. Examples of useful diazotizable amines are given in Table I. Examples of useful coupling components are given in Table II.

The coupling components are prepared by known techniques, for example, by reacting a N-hydroxyalkyl-1-naphthylamine with a epoxide such as ethylene, propylene or butylene oxide, followed by alkylation of the resultant N-hydroxyalkoxyalkyl-1-naphthylamine with alkyl halides, alkyl sulfates, aralkyl halides, etc. The aforementioned N-hydroxyalkyl-1-naphthylamine can also be reacted with activated vinyl compounds such as acrylonitrile to form the N-cyanoalkyloxyalkyl-1-naphthylamine coupling components.

Alternatively, the coupling components can be synthesized by the well-known Bucherer reaction, which involves the reversible replacement of a hydroxy group of a naphthol derivative by an amino group in the presence of aqueous sulfite, bisulfite or sulfurous acid, e.g. $SO_2 + H_2O$; see: Drake, Organic Reactions, Vol. I, John Wiley, N.Y., Chapter 5, 1942, p. 105.

Reaction of 1-naphthol with 1 to 2 equivalents of a primary aliphatic amine of the formula $H_2N-R_2-OR_4$, wherein $R_3$ and $R_4$ are as defined above, in the presence of aqueous sulfite or bisulfite at 120° to 150° C provides excellent yields (75% to 90%9) of high purity (>90%) product having the formula

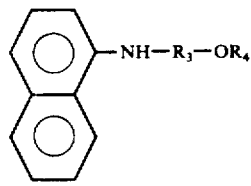

The latter process does not employ 1-naphthylamine as a starting material, a particularly desirable feature since 1-naphthylamine is an industrial carcinogen.

The primary aliphatic amines, $H_2N-R_3-OR_4$, are readily prepared by reaction of the appropriate alcohol, $R_4OH$, wherein $R_4$ is as previously defined, with acrylonitrile, methacrylonitrile or crotononitrile followed by catalytic reduction of the cyano group. Operable alcohols include cyclohexanol, methylcyclohexanol, benzyl alcohol, 2-methoxyethanol, 2-ethoxyethanoll, 1-methoxy-2-propanol, 2-propoxyethanol and 1-propoxy-2-propanol.

When the coupling component has the formula:

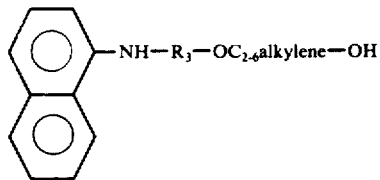

the resulting monoazo dye derived therefrom can be acylated with an acid halide or anhydride in the presence of an organic or inorganic acid acceptor, such as pyridine, trimethylamine or potassium carbonate, in a suitable organic solvent to yield the desired acylated dye.

Polar nonhydroxylic solvents, such as dimethylformamide, dimethylacetamide, dimethylsulfoxide and diethyleneglycol-dimethylether, are useful in the acylation. Pyridine is particularly useful in the acylation in that it acts as both reaction solvent and acid-binding agent. Temperatures of from 0° to 25° C are operable in the acylation, the preferred range being from 10° to 15°

C. Examples of useful acylating agents are given in Table III.

TABLE I
AMINES THAT ARE USEFUL IN THE PRESENT INVENTION

2-chloro-4,6-dinitroaniline
2-bromo-4,6-dinitroaniline
2-chloro-6-cyano-4-nitroaniline
2-bromo-6-cyano-4-nitroaniline
2,6-dicyano-4-nitroaniline
2-cyano-4,6-dinitroaniline

TABLE II
COUPLERS THAT ARE USEFUL IN THE PRESENT INVENTION

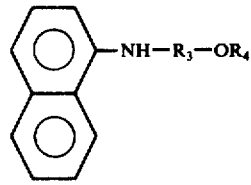

| $R_3$ | $R_4$ |
|---|---|
| $-(CH_2)_3-$ | $-C_2H_4OCH_3$ |
| $-(CH_2)_3-$ | $-CH(CH_3)CH_2OCH_3$ |
| $-(CH_2)_3-$ | $-CH(CH_3)CH_2OC_3H_{7-n}$ |
| $-(CH_2)_3-$ | ![thiophene] |
| $-(CH_2)_3-$ | $-CH_2-$ ![thiophene-O] |
| $-CH_2CH(CH_3)CH_2-$ | ![methylthiophene] |
| $-(CH_2)_3-$ | $-CH_2-$ ![furan] |
| $-(CH_2)_3-$ | $-CH_2-C_6H_5$ |
| $-C_2H_4-$ | $-C_2H_4CN$ |
| $-(CH_2)_3-$ | $-C_2H_4CN$ |
| $-CH_2CH(CH_3)CH_2-$ | $-C_2H_4CN$ |
| $-CH_2CH(CH_3)-$ | $-C_2H_4CN$ |
| $-CH_2CH(C_2H_5)-$ | $-C_2H_4CN$ |
| $-CH_2CH_2CH(CH_3)-$ | $-C_2H_4OC_2H_5$ |
| $-(CH_2)_3-$ | $-C_2H_4OC_4H_{9-n}$ |
| $-CH_2CH_2CH(CH_3)-$ | |
| | ![t-butylthiophene] |
| $-CH_2CH(CH_3)CH_2-$ | $-CH_2CH(OC_2H_5)CH_3$ |
| $-CH_2CH_2CH(CH_3)-$ | $C_2H_5$ |
| | ![thiophene] |
| $-(CH_2)_3-$ | $-CH_2CH(OCH_3)CH_2CH_3$ |
| $-(CH_2)_3-$ | $-C_2H_4OC_6H_5$ |
| $-C_2H_4-$ | $-C_2H_4OC_6H_4-(4')NO_2$ |
| $-C_2H_4-$ | $-C_2H_4OC_6H_4-(4')CH_3$ |
| $-(CH_2)_3-$ | $-C_2H_4OC_6H_4-(4')Br$ |
| $-C_2H_4-$ | $-C_2H_4OC_6H_3-(2')OCH_3,(5')CH_3$ |

TABLE III
ACYLATING AGENTS THAT ARE USEFUL IN THE PRESENT INVENTION acetic anhydride
n-butyric anhydride
propionic anhydride
benzoic anhydride
acetyl chloride

TABLE III-continued
ACYLATING AGENTS THAT ARE USEFUL IN THE PRESENT INVENTION acetyl bromide
benzoyl bromide
benzoyl chloride
2-bromobenzoyl chloride
4-bromobenzoyl chloride
p-anisoyl chloride
p-tert.-butylbenzoyl chloride
propionyl chloride
butyryl chloride
isobutyryl chloride
o-chlorobenzoyl chloride
m-chlorobenzoyl chloride
p-chlorobenzoyl chloride
2,4-dichlorobenzoyl chloride
3,4-dichlorobenzoyl chloride
3,5-dimethoxybenzoyl chloride
3,5-dinitrobenzoyl chloride
m-nitrobenzoyl chloride
p-nitrobenzoyl chloride
o-toluoyl chloride
m-toluoyl chloride
p-toluoyl chloride
m-trifluoromethylbenzoyl chloride The crude dyestuffs are conveniently converted into a commercially usable form by mixing the crude dye, e.g, ten parts on a 100% basis, with about 2.5 parts of a lignin sulfonate dispersant and water in a colloid or sand mill. Milling is continued until a fine, stable, aqueous dispersion or paste is obtained with dye particle size reduced to approximately one micron. The resultant dispersion can be vacuum or injection dried if a dry product is desired.

The invention dyes can be applied by aqueous exhaust dyeing procedures, at atmospheric pressure or a pressure above atmospheric pressure, by pad dyeing followed by dry hea fixation (e.g., Thermosol) or by printing methods from long or short baths. Such procedures are widely used in the trade and require no further explanation.

In the following Examples, all parts are given by weight. Examples 20 and 21 illustrate aqueous and Thermosol dyeing procedures, respectively. Examples 22 and 23 are directed to the printing of polyester and nylon, respectively.

EXAMPLE 1 a. A mixture of 144 parts of 1-naphthanol, 100 parts of water, 210 parts of diglycolamine ($H_2NC_2H_4OC_2H_4OH$) and 12.8 parts of sulfur dioxide was heated at 135 ± 5° C for 20 hours. Aqueous sodium hydroxide was added in an amount sufficient to form the water-soluble sodium salt of any unreacted 1-naphthol and the resulting mixture heated at 50 to 60° C for 1 hour. The crude product was extracted with benzene, and the benzene extract water-washed. Upon removal of the benzene, 190.5 parts (77.5% yield) of N-($\beta$-hydroxyethoxyethyl)-1-naphthylamine was obtained, which had a purity of 93.8%.

b. Addition was made of 2-chloro-4,6-dinitroaniline (32.5 parts), in several portions, to a stirred solution of 50.2 parts of nitrosylsulfuric acid (38% active ingredient) and 90 parts of 73% sulfuric acid at 20° to 25° C, and the mixture stirred for 3 hours. Excess nitrosylsulfuric acid was destroyed with urea. The diazo solution was then added dropwise to a cold (0 ± 5° C) aqueous methanol solution of 34.6 parts of N-($\beta$-hydroxyethoxyethyl)-1-naphthylamine. The resulting reddish-brown slurry was stirred at 0 ± 5° C for 0.5 hour, and the pH adjusted to approximately 2 by the dropwise addition of aqueous sodium hydroxide. The precipitated monoazo dye was collected by filtration, washed acid-free with water and dried to give 60.5 parts (88% yield) of product.

c. Trimethylamine (30.4 parts) was added to a cold (10° to 15° C) solution of 93.5 parts of the monoazo dye obtained in (b) above in 238 parts of dimethylformamide. Acetic anhydride (41 parts) was added dropwise over 15 minutes at 10° to 15° C. The resulting mixture was stirred for 1 hour at 10° to 15° C. The pH of the mixture was then adjusted to 5.5 by the dropwise addition of hydrochloric acid. The reaction mixture was then heated to 80° to 85° C, water was added and the mixture was allowed to cool slowly to 25° C. The precipitated solids were isolated by filtration and recrystalized from isopropanol-dimethylformamide to give 94.5 parts (93.5% yield) of bronze-colored solid, m.p. 133° to 135° C, having an absorptivity ($a_{max}$) of 85 liters $g^{-1}cm^{-1}$ at a wavelength ($\lambda_{max}$) of 612 m$\mu$. The dye was of the formula:

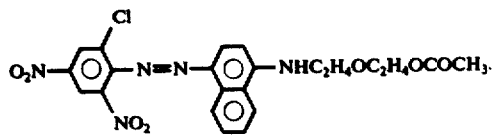

EXAMPLE 2

Benzoyl chloride (5.34 parts) was added dropwise to a cold (0° to 10° C) solution of 16.1 parts of the monoazo dye obtained in Example 1(b) above in 100 parts of pyridine. The resulting solution was stirred at 10° to 20° C for 5 hours. The dye was then precipitated by the dropwise addition of water. The resulant solids were isolated by filtration and recrystallized from isopropanol-dimethylformamide to give 17 parts of product, m.p. 183° to 186° C, having an absorptivity ($\lambda_{max}$) of 70 liters $g^{-1}cm^{-1}$ at a wavelength ($\lambda_{max}$) of 617 $\mu$u. The dye was of this formula:

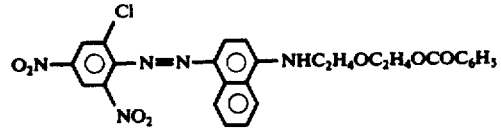

EXAMPLE 3

First, 2-chloro-4,6-dinitroaniline was diazotized as described in Example 1 paragraph (b) above and then coupled to an N-($\beta$-cyanoethyoxyethyl)-1-naphthylamine coupling component, thus providing a monoazo dye, m.p. 190° to 192° C, having an absorptivity ($a_{max}$) of 88 liters $g^{-1}cm^{-1}$ at a wavelength ($\lambda_{max}$) of 608 $\lambda$u. The dye was of this formula:

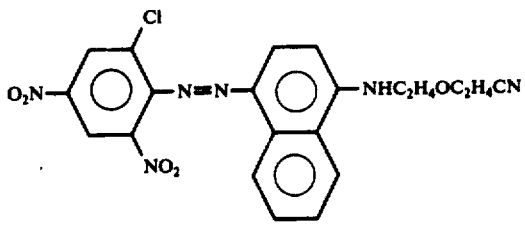

EXAMPLES 4 to 19

The dyes shown in Table IV were prepared by procedures similar to those described in Examples 1 to 3. The R groups refer to the R groups of the aforesaid general formula.

TABLE IV

| Example No. | $R_1$ | $R_2$ | $R_3$ | $R_4$ | λmax. (mμ) | $e$max $(1\ g^{-1}cm^{-1})$ |
|---|---|---|---|---|---|---|
| 4 | Cl | $NO_2$ | $-(CH_2)_3-$ | $-C_2H_4OCH_3$ | 615 | 87 |
| 5 | Cl | $NO_2$ | $-(CH_2)_3$ | $-CH(CH_3)CH_2OCH_3$ | 615 | 84 |
| 6 | Cl | $NO_2$ | $-(CH_2)_3-$ | $-CH(CH_3)CH_2OC_3H_7$-n | 615 | 82 |
| 7 | Cl | $NO_2$ | $-(CH_2)_3$ | 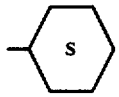 | 614 | 85 |
| 8 | Cl | $NO_2$ | $-(CH_2)_3-$ | $-CH_2C_6H_5$ | 615 | 79 |
| 9 | Cl | $NO_2$ | $-CH_2CH(CH_3)-$ | $-C_2H_4CN$ | 612 | 83 |
| 10 | Cl | $NO_2$ | $-(CH_2)_3-$ | $-C_2H_4CN$ | 613 | 94 |
| 11 | Cl | $NO_2$ | $-C_2H_4$ | $-C_2H_4OCOC_3H_7$-n | 612 | 73 |
| 12 | Br | $NO_2$ | $-C_2H_4$ | $-C_2H_4OCOCH_3$ | 612 | 85 |
| 13 | Cl | CN | $-(CH_2)_3-$ | $-C_2H_4OCH_3$ | 633 | 85 |
| 14 | Br | CN | $-(CH_2)_3-$ | $-C_2H_4OCH_3$ | 631 | 83 |
| 15 | Cl | $NO_2$ | $-(CH_2)_3-$ | $-C_2H_4OC_6H_5$ | 613 | 65 |
| 16 | Cl | $NO_2$ | $-C_2H_4-$ | $-C_2H_4OCOC_6H_4$-p-$OCH_3$ | 614 | 61 |
| 17 | Br | $NO_2$ | $-(CH_2)_3-$ | $-C_2H_4OCH_3$ | 616 | 78 |
| 18 | CN | CN | $-(CH_2)_3-$ | $-C_2H_4OCH_3$ | 665 | 128 |
| 19 | CN | $NO_2$ | $-(CH_2)_3-$ | $-C_2H_4OCH_3$ | 654 | 121 |

| | |
|---|---|
| an aqueous dye paste (15% active ingredient) containing the dye of Example 1 | 0.1 gram |
| "Avitone" T sodium hydrocarbon sulfonate (10% solution) | 1.0 ml |
| "Merpol" HCS long-chain alcohol-ethylene oxide adduct (10% solution) | 0.5 ml |
| ethylenediaminetetraacetic acid, sodium salt (1% solution) | 1.25 ml |
| butyl benzoate carrier (10% emulsion) | 1.5 ml |
| water | to 75 ml |
| acetic acid | to adjust the pH to 4.5 |

The temperature was raised to 130° C for 1 hour to effect dyeing. The dyed fabric was rinsed in water, dried and then heat-set at 135° C for 60 seconds. It exhibited a navy shade of good fastness to light and excellent fastness to sublimation.

EXAMPLE 21

THERMOSOL PROCEDURE

"Dacron" polyester/cotton blend fabric (65/35) was immersed for 15 minutes at 82° C in an aqueous bath containing 1% of a commercially available ether-alcohol sulfate surface-active agent (detergent) and 1% of tetrasodium pyrophosphate. The blend fabric was rinsed in cold water, dried and then padded at 50 to 60% pickup, based on the dry fabric weight, in a dye bath containing:

| | |
|---|---|
| an aqueous dye paste (15% active ingredient) containing the dye of Example 2 | 50 grams |
| purified natural gum thickener | 20 grams |
| water | to 1 liter. |

The padded blend fabric was passed through an infrared predryer, then heated to and held at 213° C for 90 seconds. The fabric was rinsed in water at 27° C, scoured for 5 minutes at 93° C in water containing 1% of a commercially available ether-alcohol sulfate detergent, rinsed in water at 27° C, and dried.

The dyed and scoured fabric was then permanent-press treated by padding with a pickup of 50 to 65%, based on dry fabric weight, with a bath containing:

| | g/liter |
|---|---|
| dimethyloldihydroxyethyleneurea crosslinking agent | 200.0 |
| p-octylphenoxy $(C_2H_4O)_{9-10}H$ wetting agent | 2.5 |
| dispersed acrylic thermoplastic binding agent nonionic, paraffin-free polyethylene emulsion | 22.5 |
| to serve as a fabric softener | 22.5 |
| nonionic polymer emulsion to impart luster, a silky hand and antistatic properties to the fiber | 30.0 |
| 20% aqueous zinc nitrate curing catalyst | 36.0 |

The resin-impregnated fabric was then air-dried to remove the water and cured at 163° C for 15 minutes. The polyester/cotton blend fabric was dyed to an attractive navy-blue shade having excellent fastness to sublimation.

EXAMPLE 22

PRINTING ON POLYESTER

A printing paste was prepared containing:

| | |
|---|---|
| an aqueous dye (15% active ingredient) containing the dye of Example 20 | 15.0 g |
| an etherified starch-sodium alginate thickening agent | 50.0 g |
| a phenoxyethanol-polyethylene glycol printing assistant | 8.0 g |
| monosodium phosphate (anhydrous) | 0.3 g |
| sodium chlorate | 0.5 g |
| water | to 100 grams. |

The print paste was applied from an engraved roller to polyester fabric. The printed fabric was then steamed for 1 hour at 25 psig in order to fix the dye. The fabric was then rinsed in cold water and reductively cleared at 82° C for 2 minutes in a bath containing 2 g/liter of caustic soda, 2 g/liter of hydrosulfite and 2 g/liter of a nonionic polyethylene oxide detergent. The fabric was then rinsed and dried. A strong uniformly colored blue print having excellent lightfastness was obtained.

EXAMPLE 23

PRINTING ON POLYAMIDE

A printing paste was prepared containing:

| | |
|---|---|
| an aqueous dye paste (15% active ingredient) containing the dye of Example 1 | 15.0 g |
| a natural gum thickening agent | 50.0 g |
| citric acid | 0.3 g |
| urea | 5.0 g |

-continued

| | |
|---|---|
| sodium chlorate | 0.3 g |
| p-chlorophenoxyethanol carrier | 2.0 g |
| water | to 100 grams. |

The print paste was roller printed on polyamide derived from bis(p-aminocyclohexyl)methane and dodecanedioic acid. Said polyamide is described more fully in coassigned U.S. Pat. No. 3,393,210, and is sold under the trademark "Quiana". The printed fabric was steamed for 1 hour at 22 psig and then scoured at 82° C for 2 minutes in a bath containing 2 g/liter of caustic soda, 2 g/liter of hydrosulfite and 2 g/liter of a nonionic polyethylene oxide detergent. The fabric was finally rinsed and dried. A deep navy-blue print was obtained.

The embodiments of the invention in which an exclusive property or privilege is claimed are defined as follows:

1. The dye having the formula

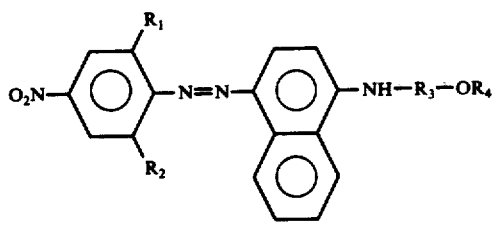

wherein
$R_1$ is Br, Cl or CN;
$R_2$ is CN or $NO_2$;
$R_3$ is $C_{2-4}$alkylene;
$R_4$ is $C_{2-6}$alkylene-$R_5$;
$R_5$ is $-OCOC_{1-4}$alkyl or $-OCOR_6$; and
$R_6$ is phenyl or phenyl substituted with 1-2 groups selected from Cl, Br, $NO_2$, $C_{1-4}$alkyl, $O-C_{1-4}$alkyl and $CF_3$.

2. The dye of claim 1 having the formula

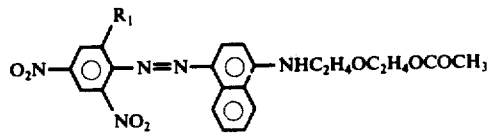

wherein $R_1$ is Cl or Br.

3. The dye of claim 2 wherein $R_1$ is Cl.
4. The dye of claim 2 wherein $R_1$ is Br.
5. The dye of claim 1 having the formula

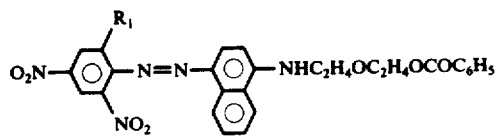

wherein $R_1$ is Cl or Br.

6. The dye of claim 5 wherein $R_1$ is Cl.
7. The dye of claim 5 wherein $R_1$ is Br.
8. The dye of claim 1 having the formula

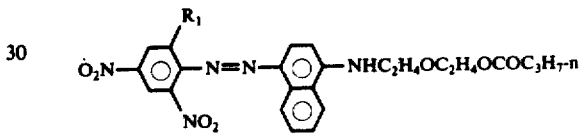

wherein $R_1$ is Cl or Br.

9. The dye of claim 8 wherein $R_1$ is Cl.
10. The dye of claim 8 wherein $R_1$ is Br.